United States Patent [19]
Kleihues

[11] Patent Number: 5,797,936
[45] Date of Patent: Aug. 25, 1998

[54] MICROSURGICAL INSTRUMENT

[76] Inventor: Hein Kleihues, Carmerstr. 4, Berlin, Germany, D-10623

[21] Appl. No.: 669,367

[22] PCT Filed: Dec. 30, 1994

[86] PCT No.: PCT/DE94/01553

§ 371 Date: Sep. 18, 1996

§ 102(e) Date: Sep. 18, 1996

[87] PCT Pub. No.: WO95/18573

PCT Pub. Date: Jul. 13, 1995

[30] Foreign Application Priority Data

Jan. 5, 1994 [DE] Germany ............... 44 00 409.5

[51] Int. Cl.$^6$ ................................................ A61B 17/32
[52] U.S. Cl. ................................. 606/167; 606/170
[58] Field of Search ........................... 606/167, 170, 606/180, 171, 159

[56] References Cited

U.S. PATENT DOCUMENTS 5,217,460  6/1993  Knoepfler ....................... 606/170
5,620,453  4/1997  Nallakrishnan ................. 606/167

*Primary Examiner*—Michael Buiz
*Assistant Examiner*—Kevin Truong
*Attorney, Agent, or Firm*—Evenson, McKeown, Edwards & Lenahan, P.L.L.C.

[57] ABSTRACT

Microsurgery instrument particularly for surgical endoscopy/arthroscopy has a first jaw part which protrudes from the distal end of a hollow shaft connected on its other end with a first handle part, and which is stationary on the hollow shaft. A second jaw part is swivellably arranged and can be actuated by a first connecting rod extending through the hollow shaft, by way of a second handle part provided on its other hand, in order to carry out a gripping or clamping operation. On the distal end of the hollow shaft, a cutting device is provided which can be actuated by a third handle part by way of a second connecting rod which is axially displaceable in the hollow shaft to carry out a cutting operation on the gripped tissue section.

15 Claims, 5 Drawing Sheets

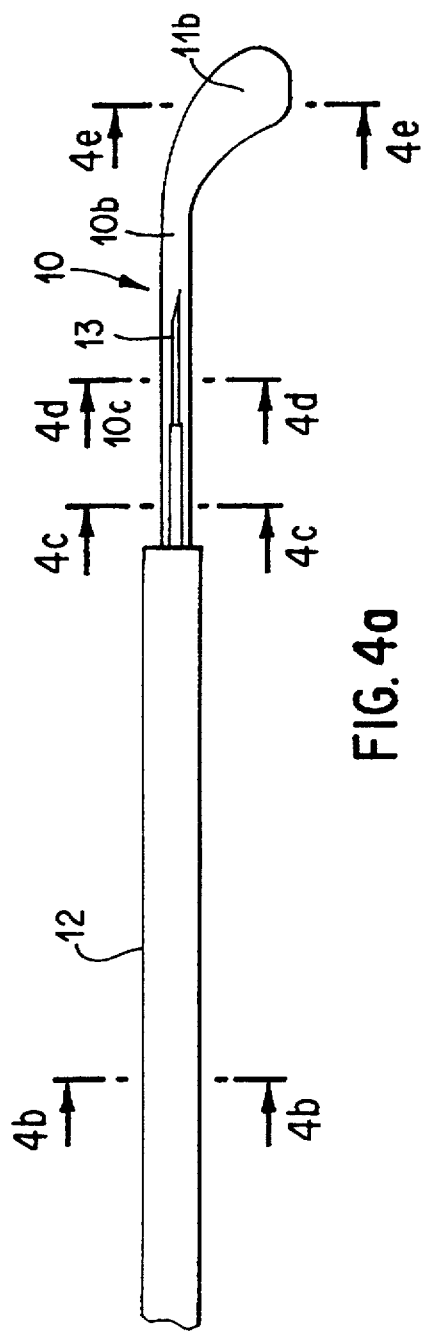
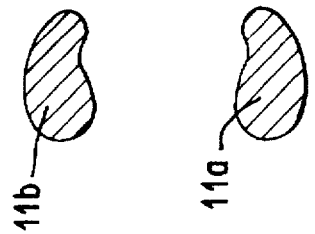
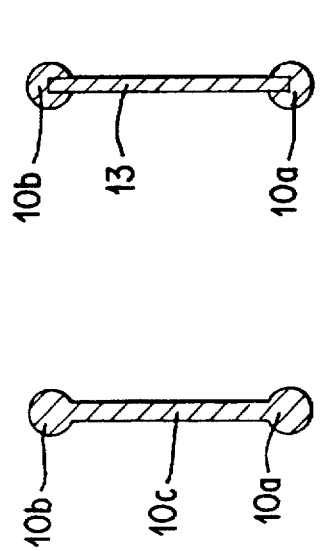
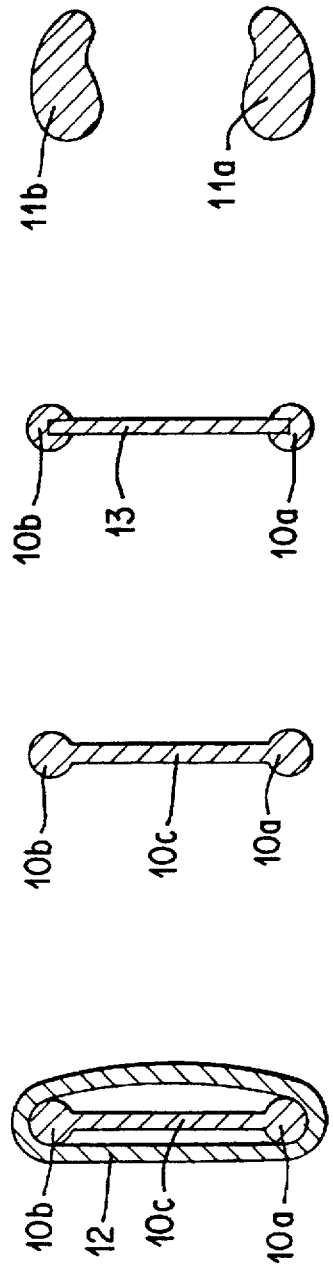

MICROSURGICAL INSTRUMENT

BACKGROUND AND SUMMARY OF THE INVENTION

This application claims the priority of German application PCT/DE 94/01553 and P 44 00 409.5, the disclosures of which are expressly incorporated by reference herein.

The present invention relates to a microsurgery instrument, and more particularly, to a microsurgery instrument for surgical endoscopy/arthroscopy, having a first jaw part which protrudes from the distal end of a hollow shaft connected on its other end with a first handle part, and which is stationary on the hollow shaft, as well as having a second jaw part which is swivellably arranged on it and which can be actuated by means of a first connecting rod extending through the hollow shaft, by way of a second handle part provided on its other hand, in order to carry out a gripping or clamping operation.

In surgery, minimally invasive (microsurgical) operating methods and the instruments suitable for this purpose are gaining more and more importance. Their use is also proven mainly in arthroscopy. However, it is also becoming more and more established in other fields—such as abdominal surgery.

Thus, in the case of injuries of the meniscus in which a removal of the meniscus is unavoidable, it is known to carry out this removal by instruments which are advanced through a narrow transcutaneous opening in the area of the knee joint to the injured meniscus or to the rear wall of the capsule.

In a first operating phase—which in itself already consists of several steps—, by way of punching forceps or by way of a hooked punch, as it is described approximately in DE 38 02 907 A1 (in a special construction having a suction device), the meniscus is perforated along its base by adjoining punchings. This operating phase is terminated shortly before the meniscus is completely separated in this manner from the rear wall of the capsule. Now, instead of the punching forceps, the distal end of gripping forceps is introduced, as it is described approximately (in a special construction with an additional endoscope) in DE 37 38 692 A1, and the meniscus is gripped by thereby, is torn off the rear wall of the capsule and is removed from the knee joint. Finally, in a third operating phase, by way of another instrument, the rear wall of the capsule is smoothed in the area of the perforations carried out in the first operation.

This described approach requires a lot of time and, because of the necessity of intracorporally positioning several instruments successively in an exact coordination with the respective preceding operating phase, results specific sources of errors and thus in potential risks to the patient. The providing, sterilization and handling of several different instruments requires high expenditures of material and is cumbersome.

Also, in the case of appendectomies and gall bladder operations, surgery is increasingly carried out endoscopically which results in the necessity of ligating and severing vessels.

In this case, in a first and second operating step, by way of special forceps—so-called ligature forceps—vessel closing elements (ligature clips) are first arranged on both sides of an intended severing point on the vessel by way of which this vessel is permanently closed. Then, in a third operating step, a suitable device—such as microsurgery scissors according to DE 38 08 877 A1—severs the vessel between the ligature clips.

This approach, which again requires several operating steps and two different instruments, has the above-mentioned disadvantages.

The invention is therefore based on the object of providing a microsurgery instrument which, during the described and similar operations, permits a shortening of the operating time and simultaneously results in a simplification and a reduction of the number of potential sources of errors.

This object is achieved by a microsurgery instrument on the distal end of the hollow shaft, a cutting device is provided which can be actuated by way of a third handle part by means of a second connecting rod which is axially displaceable in the hollow shaft, in order to, in addition to the gripping or clamping operation, carry out a cutting operation on the gripped tissue section.

The present invention provides a microsurgery instrument which permits the carrying out of the functions of gripping or clamping (a tissue part, vessel, or similar part) and of producing a cut in this part, particularly its severing, by way of one and the same instrument and therefore in one operating phase and which combines the corresponding function elements.

The present invention is based on known endoscopically usable or microsurgery instruments, in the case of which the function of gripping, clamping or punching is carried out by two forceps parts or punching forceps parts which can be swivelled with respect to one another by way of suitable handle elements and adds to this operating principle that of a translational cutting operation which is controlled by means of another handle element. A close functional relationship exists between the two operating phases in that, during the cutting, the being gripped or clamped of the tissue part or vessel to be cut and simultaneously the positioning for the cutting device furnished by the forceps parts is utilized.

In addition to the advantage that the previous successive operating steps of the gripping or clamping and of the cutting, which required the introduction of separate instruments, can now be carried out almost simultaneously after a single introduction of one and the same instrument, this also decisively reduces the danger of positioning errors or of a "losing" of a severed tissue part (such as a severed meniscus in the knee joint).

In an advantageous construction, the cutting device has a cutting blade disposed between two guide rods or guide wires, which can be moved out axially with respect to the distal end of the exterior shaft laterally of the jaw parts of the gripping or clamping device, and which cutting blade can be displaced with the guide rods or guide wires essentially in the same direction.

Particularly for the use of the instrument in arthroscopy—specifically, for example, for the severing of a meniscus from the concavely curved rear wall of the knee joint capsule—it is advantageous for the guide rods or guide wires to be constructed to be flexible in the partially and completely moved-out condition perpendicularly to their longitudinal axis, and to be constructed to be bendable particularly in the direction of the jaw parts. The reason is that they can then describe a curved path along a curved contact surface and therefore permit such a cut.

The instrument as a whole can also have a curved shape in order to facilitate the handling in body cavities, joints, etc.

The cutting blade can be fixedly connected with the guide rods but basically can also be displaceable with respect thereto. The former is constructively simpler, the latter makes it possible to first determine, examine and possibly correct the cutting plane by the moving out of the guides and to only then carry out the cut.

The cutting device can have a purely mechanically operating blade—for example, made of special steel or of another metal and optionally with a sliding coating—or it can have an electric cauterizing knife. In the latter case, simultaneously with the cut, a tissue coagulation is achieved in an advantageous manner on the cut surfaces.

For avoiding undesirable tissue or vessel perforations, it is advantageous—particularly when the cutting device is to be used on curved contact surfaces (joint capsules or the like)—for the guide rods or guide wires to have in each case a distally arranged rounded protecting cap. In the case of a special design of the instrument for a specific use—such as cutting off the meniscus—the shape of the protecting cap can be adapted to it.

The introduction of the instrument into the body can be facilitated and injuries during the introduction can be avoided if the forceps parts or jaw parts each have a recess which corresponds to the design of the protecting caps. Thereby, in the moved-in condition of the cutting device and when the forceps parts are closed, the protecting caps are accommodated such that the distal end of the instrument for being introduced into the body has a closed, convexly curved surface. In addition, it is advantageous for the protecting caps and/or the recesses to have a locking device which, in the moved-in condition, locks the protecting caps with the forceps parts. Even when there is resistance during the introduction, these cannot be pressed out of the recesses.

A particularly cost-saving embodiment consists of constructing the cutting device to be detachable from the rest of the instrument and to be exchangeable. It can then be produced, on the one hand, in the same standardized shape for differently designed instruments and can, on the other hand, be exchanged as a (low-cost) component part when it is worn.

Another advantageous construction of the instrument, which also permits construction kit solutions, consists of constructing the exterior shaft in two parts at least in a distal section of its longitudinal course. That is, the first connecting rod is accommodated in the first part and the second connecting rod and the cutting device is accommodated in the second part, and at least one distal section of the second part of the exterior shaft together with the cutting device is constructed to be detachable from the remaining instrument and is exchangeable.

The solution according to the invention can be used widely in many fields of microsurgery. In particular, it can represent clip forceps for mounting ligature clips for the permanent closing of a vessel and simultaneously for the severing of the closed vessel or it can represent meniscus gripping forceps with an integrated meniscotomy knife.

BRIEF DESCRIPTION OF THE DRAWINGS

Other objects, advantages and novel features of the present invention will become apparent from the following detailed description of the invention when considered in conjunction with the accompanying drawings wherein:

FIGS. 4a to 4e are representations of details of an embodiment of the cutting device of the instrument according to the invention.

DETAILED DESCRIPTION OF THE DRAWINGS

Figure 1:
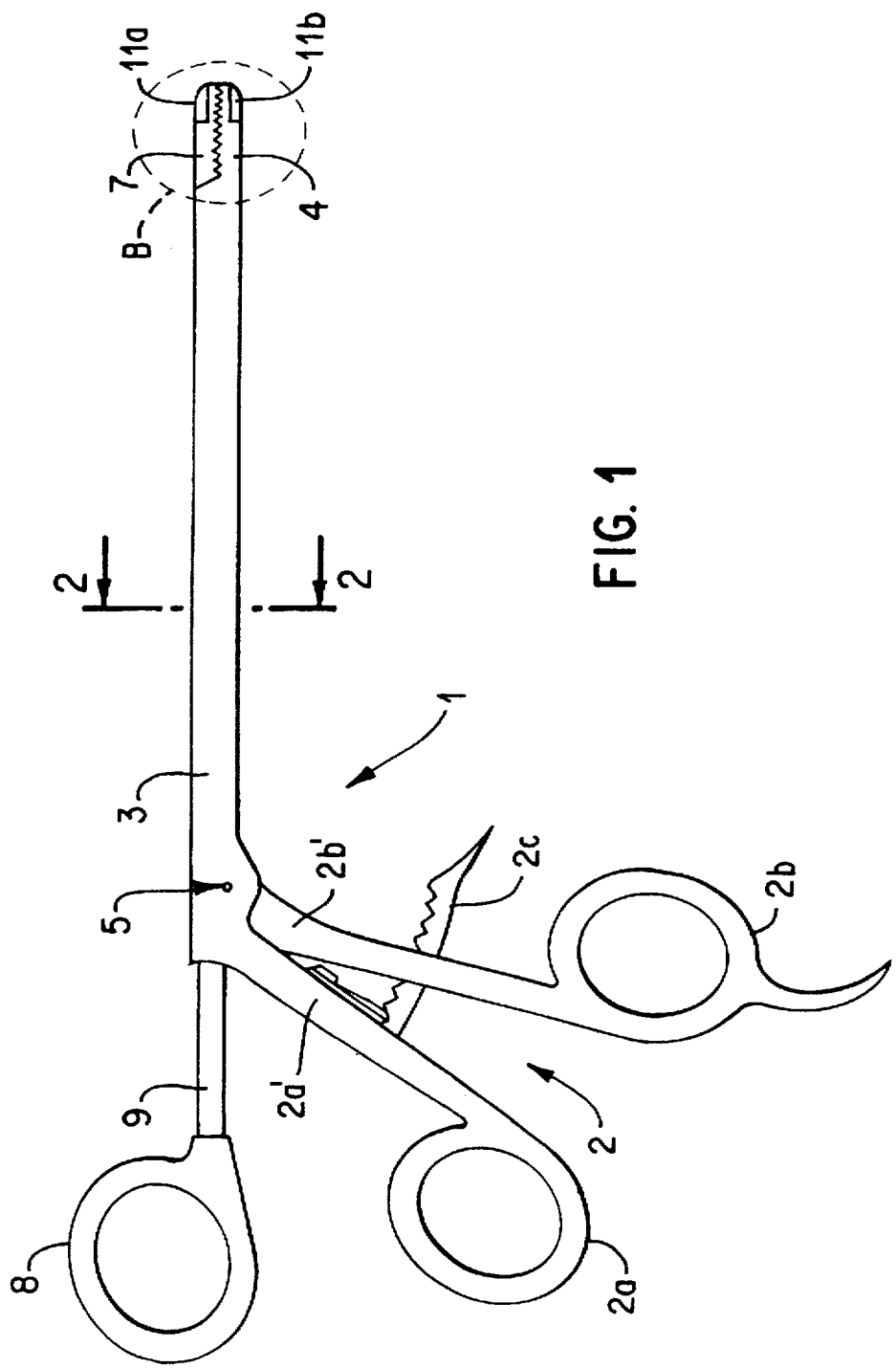
FIG. 1 is a side view of an embodiment of the instrument according to the invention.

FIG. 1 is an embodiment of the instrument according to the invention in the form of meniscus gripping forceps with an integrated meniscotomy knife.

The meniscus gripping forceps 1 has a scissors handle 2 with two handle pieces 2a and 2b as well as a locking latch 2c for the actuating. The first scissors handle piece 2a leads on its front end 2a' into an approximately hollow cylindrical shaft 3 which, on its distal end, ends in a first jaw part 4. The second scissors handle piece 2b, on its front end 2b', distally from an axis of rotation 5 disposed in the shaft 3, is connected with a first connecting rod 6 (not shown in FIG. 1 but visible in FIG. 2) which carries a second jaw part 7 on its distal end, which jaw part 7 has a second (not shown) axis of rotation. By way of a movement of the second handle piece 2b relative to the first handle piece 2a, which is translated by the two axes of rotation and the connecting rod 6 and is transmitted to the second jaw part 7, the second jaw part 7 can be swivelled with respect to the first jaw part 4 and can be locked by way of the locking latch 2c in the taken-up position.

In addition to the scissors handle 2 with its two handle pieces 2a, 2b, the meniscus gripping forceps according to FIG. 1 has another third handle piece 8 which forms the proximal end of a second connecting rod 9. On its distal end, a cutting device 10 is mounted which is shown in greater detail in FIG. 3 and of which only end cams 11a and 11b can be seen in FIG. 1.

Figure 2:
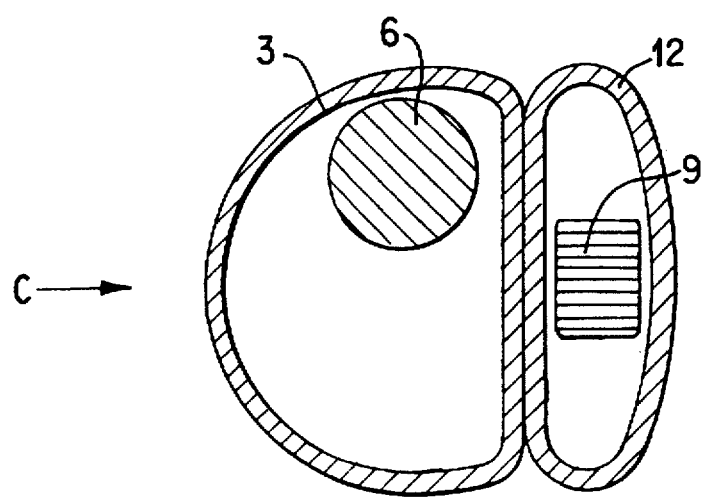
FIG. 2 is a schematic cross-sectional view in plane A—A' of the embodiment illustrated in FIG. 1.

FIG. 2 is a schematic cross-sectional view of the shaft arrangement of the meniscus gripping forceps 1 illustrated in FIG. 1 in the intersection plane A—A' marked in FIG. 1. The viewing direction of FIG. 1 is indicated by the arrow C in FIG. 2.

The first connecting rod 6 arranged in the (first) hollow shaft 3 actuated the second jaw part. Furthermore, the second connecting rod 9 for actuating the cutting device is arranged in a separate second hollow shaft 12 which is fixedly connected with the hollow shaft 3.

Figure 3:
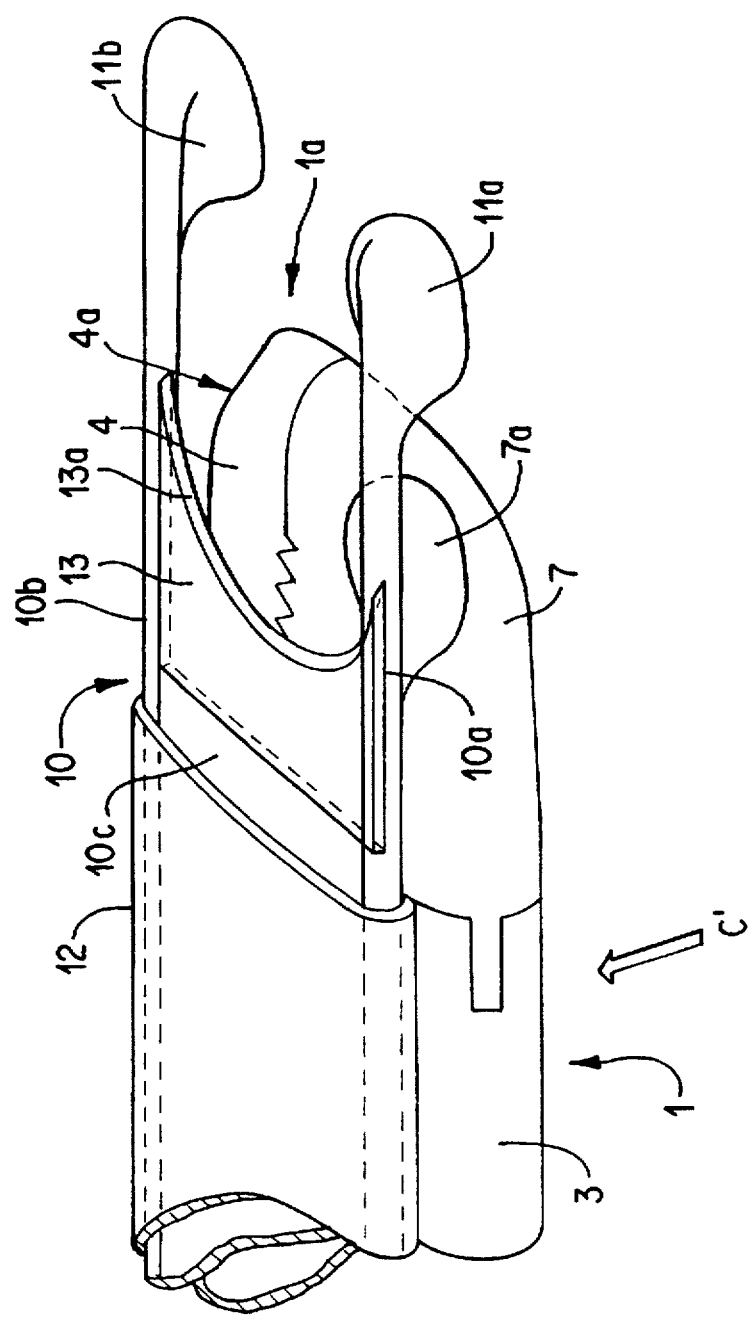
FIG. 3 is a perspective representation of the distal area B of the embodiment illustrated in FIG. 1.

FIG. 3 is a perspective representation of the distal section of the meniscus gripping forceps 1 marked in FIG. 1 with the letter "B", viewed from the direction of the upper edge of the meniscus gripping forceps 1 diagonally toward the rear side, with a half-extended cutting device 10. (The viewing direction on which FIG. 1 is based is indicated by the arrow C' in FIG. 3.)

The left side of FIG. 3 again shows the arrangement of the two hollow shafts 3 and 12, in which case, at this point in the hollow shaft 12, the second connecting rod 9 is no longer shown but the cutting device 10 is already shown in a cross-sectional view which is distally connected therewith.

The cutting device 10, which is displaceable in the interior of the second hollow shaft 12, is detachably connected with the second connecting rod 12 and can therefore be exchanged, has two lateral, bendable plastic guide rods 10a and 10b and a web 10c connecting them. The guide rods 10a and 10b end distally in one cam-type thickened part or protecting cap 11a and 11b respectively. In their distal area which is rounded to form a common, convexly curved frontal surface 1a of the gripping forceps 1, the first and the second jaw part 4 and 7 each have a recess 4a and 7a which is adapted to the shape of the thickenings 11a and 11b and in which the thickenings rest in the completely retracted condition of the cutting device 10.

Distally from the web 10c and in an arrangement continuing it, a special-steel cutting blade 13 is fastened with a front edge 13a which is chamfered between the guide rods 10a and 10b and is simultaneously concavely curved. The front edge 13a has a distance of a few millimeters from the thickenings 11a and 11b and is chamfered or ground in the direction of the jaw parts 4 and 7.

In detailed representations, FIGS. 4a to 4e again show in a lateral view and four cross-sectional views the construction of the cutting device 10 in the second hollow shaft 12. FIGS. 4b to 4e are cross-sectional representations in the intersection planes of the lateral view according to FIG. 4a marked by arrows b, b', c, c', d, d' and e, e'.

The parts and the pertaining reference numbers are the same as in FIG. 3, so that the description does not have to be repeated here.

In the following, the method of operation will be described of the meniscus gripping forceps with the integrated microtome illustrated in FIGS. 1 to 3.

First, while the jaw parts 4 and 7 are closed and the protecting caps 11a and 11b are completely lowered into the recesses 4a and 7a, the instrument is positioned in the conventional manner through a transcutaneous access in the area of the knee joint. Then, by actuating the scissors handle 2, the jaw parts 4 and 7 are swivelled apart, are guided around the meniscus to be removed, and the meniscus is gripped by the folding-together of the jaw parts.

Then, by way of the handle piece 8 and by way of the connecting rod 9, the cutting device 10 is advanced, in which case the guide rods 10a and 10b slide around the meniscus base on the concavely curved rearward capsule wall and determine an identically curved cutting plane for the cutting blade 13. The cutting blade, which follows the distal thickenings 11a and 11b at a constructively determined distance and is sufficiently flexible in the longitudinal direction,— following the indicated cutting plane—severs the meniscus on its base from the capsule wall, in which case it remains gripped between the jaw parts 4 and 7 and, after the severing, can be removed together with the instrument.

The cam-type thickenings or protecting caps 11a and 11b , together with the flexibility of the cutting device, permit a relatively easy sliding of the guide rods 10a and 10b on the capsule wall without the risk of penetrating into it and thus of a catching of the cutting device. During the severing operation, the chamfered configuration of the cutting blade advantageously permits a precise cut which requires little force, while an agglomeration of tissue on one of the guide rods is avoided. A sliding coating of the cutting blade additionally facilitates the cutting. The severing can additionally be promoted by a pulling on the meniscus gripped during the cutting by the jaw parts.

The described approach requires much lower expenditures with respect to time and instruments and has fewer risks than the conventional surgical approach.

The implementation of the invention is not limited to the above-described preferred embodiment. On the contrary, a number of variants are conceivable which use the illustrated solution also in the case of different types of embodiments.

Particularly, multi-design modifications of the shape of the entire instrument—which, in an adaptation to special purposes can be curved in the longitudinal and/or transverse direction—as well as of the actuating elements—which can simulate forceps handles or T-shaped pressure pieces—of the jaw parts and of the cutting device can be implemented.

Two correspondingly modified embodiments are outlined in FIGS. 5a to 5d and 5e and 5f.

Figure 5A:
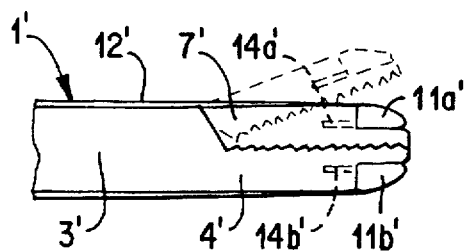
FIGS. 5a to 5f are representations of details of embodiments of the invention modified with respect to FIG. 1.
Figure 5C:
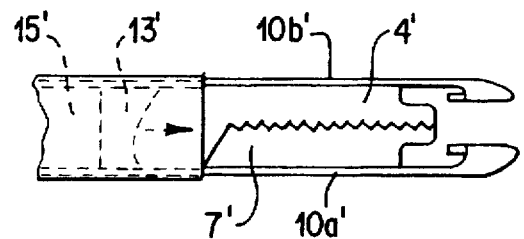
Figure 5B:
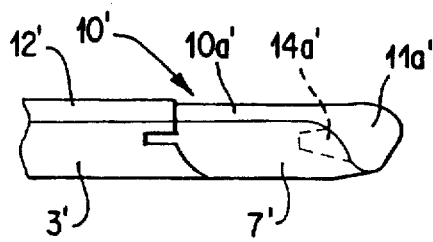
Figure 5D:
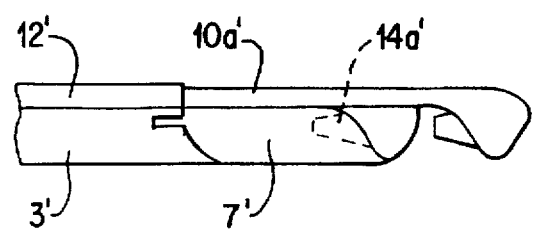

The embodiment shown in FIG. 5a corresponding to the viewing direction of FIG. 1; shown in FIG. 5c from the opposite side; and shown in FIG. 5b and 5d from the top edge of the gripping forceps, has the same main components as the one described in FIGS. 1 to 3. The main components are indicated by the corresponding, one-prime reference numbers and will not be described again in the following. FIGS. 5a and 5b show the instrument with a retracted cutting device and FIGS. 5c and 5d show the instrument with a partially extended cutting device.

The instrument differs from the instrument according to FIGS. 1 to 3 by the changed shape of the jaw parts 4' and 7' and of the cams or protecting caps 11a' and 11b' which here have proximally directed locking pins 14a' and 14b' which, in the retracted condition of the cutting device 10', rest in corresponding recesses in the jaw parts 4' and 7' and lock the guide rods 10a' and 10b' laterally on all sides.

It also differs from the gripping forceps according to FIGS. 1 to 3 in that—as indicated in FIG. 5c—the cutting blade 13' is not fixedly connected with the guide rods 10a' and 10b' but is displaceably guided between these and can be advanced by way of a separate pressure piece 15' after the guide rods were moved out first.

Figure 5E:
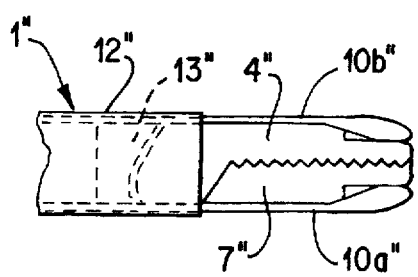
Figure 5F:
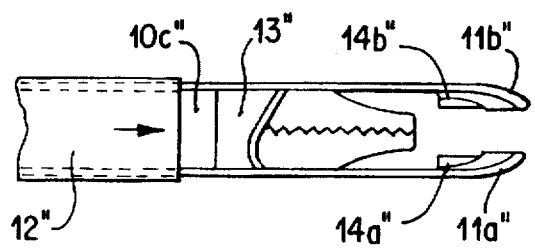

In a corresponding representation of details, FIGS. 5e and 5f show another embodiment from a viewing direction which is opposite the viewing direction of FIG. 1, with a retracted (FIG. 5e) and a partially extended cutting device (FIG. 5f). Here also, the main parts correspond to those of FIGS. 1 to 3, are marked correspondingly (two primes) and will not be explained again. In this case, coiled spring steel guide wires 10a" and 10b" have replaced the plastic guide rods; the cutting blade 13" is welded to these guide wires; and plastic caps 11a" and 11b" with locking nubs 14a" and 14b" are pressed onto the front end. Corresponding to their shape, recesses are again provided in the jaw parts 4' and 7'. In a manner which is not shown in the representations of the details, in this embodiment, the cutting device 10", including the hollow shaft 12" accommodating and guiding it, is connected with the remaining instrument by a clamped or screwed connection and can be exchanged.

When the invention is constructed as meniscus gripping forceps or, more generally, for arthroscopic applications, it may be expedient to manufacture separately left-cutting and right-cutting configurations which have an arrangement and construction of the cutting device which is mutually mirror-symmetrical with respect to the vertical plane of the instrument.

Embodiments for closing and severing vessels in abdominal surgery, preferably have a forceps part which is constructed for placing ligature clips—and is known as such— as well as a cutting device which has a modified construction in comparison to the meniscotome. Since, in this case, the guide rods or wires do not have to slide along a curved surface but must slide approximately around the exterior wall of a vessel, particularly the shape of the thickenings and possibly also the bending characteristics of the guide rods may deviate from the above-described examples.

A correspondingly adapted electric cauterizing knife can also be provided as the cutting device.

Also with respect to the selection of material, the explained embodiments must be understood as expedient examples. Materials can also be used which are proven in medical technology for comparable applications.

Although the invention has been described and illustrated in detail, it is to be clearly understood that the same is by way of illustration and example, and is not to be taken by way of limitation. The spirit and scope of the present invention are to be limited only by the terms of the appended claims.

I claim:

1. Microsurgery instrument for surgical procedures, comprising a hollow shaft, a first jaw part which protrudes from a distal end of the hollow shaft a first handle part stationarily connected on another end of the hollow shaft., a second jaw part swivellably arranged at the hollow shaft, a first connecting rod extending through the hollow shaft for actuating the second jaw part via a second handle part provided on the another end to carry out a gripping or clamping operation of a tissue section, wherein, on the distal end of the hollow shaft, a cutting device is operatively actuatable via a third handle part associated with a second connecting rod axially displaceable in the hollow shaft, to perform a cutting operation on the gripped or clamped tissue section.

2. Microsurgery instrument according to claim 1, wherein the cutting device has a cutting blade disposed between two guide rods or guide wires arranged to be axially moved out with respect to the distal end of the hollow shaft laterally of the first and second jaw parts displaceable therewith substantially in the same direction.

3. Microsurgery instrument according to claim 2, wherein the guide rods or wires, in a partially and in a completely moved-out condition, are constructed to be flexible perpendicularly to a longitudinal axis thereof, and are bendable in the direction of the first and second jaw parts.

4. Microsurgery instrument according to claim 3, wherein the cutting blade is fixedly connected with the guide rods or wires, with a front edge thereof having a distance from distal ends of the guide rods or wires.

5. Microsurgery instrument according to claim 2, wherein the cutting blade is provided with ground surface in the direction of the first and second jaw parts.

6. Microsurgery instrument according to claim 2, wherein the cutting blade has a concavely curved front edge.

7. Microsurgery instrument according to claim 2, wherein the cutting device has an electric cauterizing knife.

8. Microsurgery instrument according to claim 2, wherein the guide rods or wires each have a distally arranged, rounded thickened portion.

9. Microsurgery instrument according to claim 8, wherein the first and the second jaw parts each have a recess which corresponds to the shape of the thickened portions and in which, in a retracted condition of the cutting device with the jaw parts closed, the thickened portions are configured and arranged to be accommodated such that, for the introduction into a body, the instrument has a closed, convexly curved surface.

10. Microsurgery instrument according to claim 9, wherein at least one of the thickened portions and the recesses have a locking device configured to lock the thickened portions in the retracted condition with the first and second jaw parts.

11. Microsurgery instrument according to claim 2, wherein the cutting device is configured to be detachable from the hollow shaft.

12. Microsurgical instrument according to claim 1, wherein the hollow shaft is constructed in two parts at least in a distal section of its longitudinal course, the first connecting rod being accommodated in a first of the two parts and and the second connecting rod and the cutting device being accommodated in the second of the two parts.

13. Microsurgery instrument according to claim 12, wherein at least a distal section of the second part of the hollow shaft and the cutting device is detachably and exchangably configured.

14. Microsurgery instrument according to claim 1, wherein the first and the second jaw parts comprise a clip forceps for mounting ligature clips for permanent closing of vessels.

15. Microsurgery instrument according to claim 1, wherein the first and the second jaw parts comprise a meniscus gripping forceps.

* * * * *